United States Patent [19]

Iijima et al.

[11] Patent Number: 4,840,886
[45] Date of Patent: Jun. 20, 1989

[54] SILVER HALIDE COLOR PHOTOGRAPHIC MATERIAL CONTAINING A 1H-PYRAZOLE (3,2-C)-S-TRIAZOLE DERIVED MAGENTA COUPLER

[75] Inventors: Toshifumi Iijima; Kenji Kumashiro; Hiroshi Kashiwagi; Koichi Hatta; Yuji Hotta; Hiroko Ohya; Noritaka Nakayama; Satoshi Kawakatsu; Katsunori Katoh; Kaoru Shinozaki, all of Tokyo, Japan

[73] Assignee: Konishiroku Photo Industry Co., Ltd., Japan

[21] Appl. No.: 161,321

[22] Filed: Feb. 26, 1988

Related U.S. Application Data

[63] Continuation of Ser. No. 086,188, Aug. 14, 1987, abandoned, which is a continuation of Ser. No. 775,685, Sep. 13, 1985, abandoned.

[30] Foreign Application Priority Data

| | | | |
|---|---|---|---|
| Sep. 14, 1984 | [JP] | Japan | 59-193609 |
| Sep. 17, 1984 | [JP] | Japan | 59-195234 |
| Nov. 15, 1984 | [JP] | Japan | 59-243012 |
| Nov. 15, 1984 | [JP] | Japan | 59-243015 |
| Apr. 3, 1985 | [JP] | Japan | 60-70198 |

[51] Int. Cl.$^4$ .................. G03C 1/08; G03C 7/26; G03C 7/32; G03C 1/46
[52] U.S. Cl. .................. 430/558; 430/386; 430/502; 430/505; 430/543; 430/554; 430/555
[58] Field of Search ............ 430/386, 543, 558, 554, 430/555, 502, 505

[56] References Cited

U.S. PATENT DOCUMENTS

| | | | |
|---|---|---|---|
| 2,322,027 | 6/1943 | Jelly et al. | 430/558 |
| 2,353,754 | 7/1944 | Peterson | 95/6 |
| 3,705,896 | 12/1972 | Bailey | 260/240 |
| 3,725,067 | 4/1973 | Bailey et al. | 430/558 |
| 3,758,309 | 9/1973 | Bailey et al. | 96/136 |
| 4,338,393 | 7/1982 | Bailey et al. | 430/386 |
| 4,456,681 | 6/1984 | Kadowaki et al. | 430/505 |
| 4,481,268 | 11/1984 | Bailey et al. | 430/17 |
| 4,500,630 | 2/1985 | Sato et al. | 430/558 |
| 4,510,234 | 4/1985 | Matsuzaka et al. | 430/557 |
| 4,529,691 | 7/1985 | Renner et al. | 430/556 |
| 4,540,654 | 9/1985 | Sato et al. | 430/381 |
| 4,548,899 | 10/1985 | Nakayama et al. | 430/386 |
| 4,562,146 | 12/1985 | Masuda et al. | 430/558 |
| 4,576,910 | 3/1986 | Hirano et al. | 430/548 |
| 4,581,326 | 4/1986 | Katoh et al. | 430/558 |
| 4,585,732 | 4/1986 | Kawagishi et al. | 430/558 |
| 4,590,153 | 5/1986 | Kawagishi et al. | 430/551 |
| 4,600,688 | 7/1986 | Kawakatsu et al. | 430/558 |
| 4,607,002 | 8/1986 | Nakayama et al. | 430/558 |
| 4,623,617 | 11/1986 | Kaneko et al. | 430/551 |
| 4,639,413 | 1/1987 | Kawagishi et al. | 430/546 |
| 4,639,415 | 1/1987 | Kaneko et al. | 430/558 |
| 4,665,015 | 5/1987 | Iijima et al. | 430/558 |
| 4,659,652 | 4/1987 | Kawagishi et al. | 430/558 |
| 4,675,280 | 6/1987 | Kaneko et al. | 430/558 |
| 4,695,533 | 9/1987 | Nakayama et al. | 430/558 |

FOREIGN PATENT DOCUMENTS

| | | | |
|---|---|---|---|
| 00723636 | 8/1982 | European Pat. Off. | |
| 0073636 | 9/1983 | European Pat. Off. | |
| 0143570 | 6/1985 | European Pat. Off. | 430/558 |
| 0177765 | 9/1985 | European Pat. Off. | |
| 0178789 | 9/1985 | European Pat. Off. | |
| 1810464 | 7/1969 | Fed. Rep. of Germany | |
| 3339201 | 5/1984 | Fed. Rep. of Germany | |
| 1247493 | 9/1971 | United Kingdom | |
| 1252418 | 11/1971 | United Kingdom | |
| 1334515 | 10/1973 | United Kingdom | |
| 2132783 | 7/1984 | United Kingdom | |
| 2135788 | 9/1984 | United Kingdom | |

OTHER PUBLICATIONS

Bailey et al., "Synthesis of 1H-pyrazolo [3,2-C]-S-Triazoles and Derived Azamethine Dyes", J. Chem. Soc. Perkin I., 18, 1977, pp. 2047-2052.
Research Disclosure 12443, published Aug. 1974.
Research Disclosure 20525, published May 1981, p. 184.
Research Disclosure 20919, published Sept. 1981, pp. 345-346.
Examiner's Report for EPO Pat. Appln. No. 85 306569.6, dated 4/9/87.

Primary Examiner—Mukund J. Shah
Attorney, Agent, or Firm—Finnegan, Henderson, Farabow, Garrett & Dunner

[57] ABSTRACT

A silver halide color photographic material having at least one silver halide emulsion layer on a support is disclosed. Said silver halide emulsion layer contains at least one of the 1H-pyrazolo [3,2-c]-S-triazole derived magenta couplers that have a substituent of the following formula at 3-position:

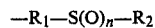

$$-R_1-S(O)_n-R_2$$

wherein
$R_1$ is an alkylene group;
$R_2$ is an alkyl, cycloalkyl or aryl group; and
n is 1 or 2.

11 Claims, No Drawings

SILVER HALIDE COLOR PHOTOGRAPHIC MATERIAL CONTAINING A 1H-PYRAZOLE (3,2-C)-S-TRIAZOLE DERIVED MAGENTA COUPLER

This application is a continuation of application Ser. No. 086,188, filed Aug. 14, 1987, now abandoned which in turn is a continuation of application Ser. No. 775,685, filed Sept. 13, 1985 now abandoned.

FIELD OF THE INVENTION

The present invention relates to a silver halide color photographic material that contains a magenta coupler capable of effective color formation and which forms a magenta dye image having improved keeping quality, particularly in terms of light fastness. More specifically, the invention relates to a silver halide color photographic material containing a novel 1H-pyrazolo[3,2-c]-S-triazole derived magenta coupler.

BACKGROUND OF THE INVENTION

The formation of dye images in most silver halide color photographic materials depends on the reduction of exposed silver halide grains with an aromatic primary amine color developing agent and the subsequent coupling of the resultant oxidation product of the color developing agent with couplers that respectively form yellow, magenta and cyan dyes.

Pyrazolone type couplers are commercially used as couplers for providing magenta dyes, but they have an unwanted secondary absorption and their keeping quality, particularly their resistance to formalin gas, is relatively low.

A variety of 1H-pyrazol[3,2-c]-S-triazole derived magenta couplers have been proposed to overcome these problems of the conventional pyrazolone type couplers. Reference should be had to U.S. Pat. No. 3,725,067, as well as British Pat. Nos. 1,252,418 and 1,334,515. The compounds disclosed in these patents avoid the problem of secondary absorption but the improvement is inadequate in terms of resistance to formalin gas and is insignificant in respect of the production of a light-fast magenta dye image. The compound disclosed in Research Disclosure No. 12443 has no commercial value because of its low color formation. The 1H-pyrazolo[3,2-c]-S-triazole type magenta coupler disclosed in Unexamined Published Japanese Patent Application No. 42045/1983 features significant improvements in formalin resistance and color formation but little improvement has been achieved in terms of the production of a light-fast image.

Improved color development has also been achieved by the couplers described in Unexamined Published Japanese Patent Application Nos. 99437/1984 and 125732/1984 but the dye images produced by these couplers are still low in light fastness. The coupler disclosed in Unexamined Published Japanese Patent Application No. 99437/1984 depends on the concomitant use of additives for providing a light-fast image. The coupler disclosed as Compound No. 19 in Unexamined Published Japanese Patent Application No. 125732/1984 produces a dye image having slightly improved light fastness but the improvement is far from being satisfactory.

In short, the 1H-pyrazolo[3,2-c]-S-triazole derived magenta couplers that have been considered useful because of the absence of secondary absorption and their high resistance to formalin gas fall far short of satisfying the requirement for providing dye images with improved light fastness.

SUMMARY OF THE INVENTION

One object, therefore, of the present invention is to provide a silver halide color photographic material that contains a magenta coupler capable of effective color formation and which forms a magenta dye image having improved light fastness and resistance to formalin gas.

Another object of the invention is to provide a silver halide color photographic material that forms a magenta dye having improved spectral absorption characteristics.

These objects of the invention are achieved by a silver halide color photographic material that has at least one silver halide emulsion layer on a support, said silver halide emulsion layer containing at least one of the 1H-pyrazolo[3,2-c]-S-triazole derived magenta couplers that have a substituent of the following formula at 3-position:

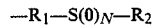

$$-R_1-S(0)_N-R_2$$

wherein
 $R_1$ is an alkylene group;
 $R_2$ is an alkyl, cycloalkyl or aryl group;
 n is 1 or 2, preferably 2.

DETAILED DESCRIPTION OF THE INVENTION

The inventors have found that compounds wherein a group represented by the above formula is substituted at 3-position of 1H-pyrazolo[3,2-c]-S-triazole will exhibit effective color formation and provide magenta dye images having improved light fastness and formalin resistance.

Further improvements in light fastness and color formation are achieved by introducing as a substituent a leaving group other than hydrogen at 7-position of 1H-pyrazolo[3,2-c]-S-triazole which is the site of coupling with the oxidation product of a color developing agent.

The alkylene group at $R_1$ may be substituted by alkyl, aryl (e.g. phenyl), halogen, cyano, a group that is bonded by carbonyl (e.g. alkoxycarbonyl, acyl or carbamoyl), or a group that is bonded by a hetero atom (e.g. nitro, alkoxy, alkylthio or dialkylamino). The alkylene group at $R_1$ preferably has 1 to 6 carbon atoms.

The alkyl group at $R_2$ includes a primary alkyl, a branched alkyl (secondary or tertiary alkyl). The primary alkyl is an alkyl having two hydrogen atoms attached to the carbon atom directly coupled to the magenta coupler of the present invention; the secondary alkyl is an alkyl having one hydrogen atom attached to the carbon having a substituent; and the tertiary alkyl is an alkyl having no hydrogen atom attached to the carbon atom directly coupled to the magenta coupler of the present invention. The alkyl group as $R_2$ may be linear or branched and preferably has 1–30 carbon atoms as illustrated by methyl, ethyl, propyl, i-propyl, butyl, 2-ethylhexyl, octyl, dodecyl, tetradecyl, hexadecyl, octadecyl and 2-hexyldecyl. An example of the cycloalkyl group as $R_2$ is cyclohexyl. The alkyl or cycloalky group represented by $R_2$ may have a substituent such as an aryl group, heterocyclic group, halogen atom or a cyano group; a substituent that is bonded by carbonyl as illustrated by alkoxycarbonyl, acyl or carbamoyl; or a substituent that is bonded by a hetero atom (e.g. O, N or S) as illustrated by nitro, alkoxy, alkylthio, alkylsulfonyl, arylsulfonyl, alkylsulfinyl, arysulfinyl or dialkylamino. If two or more of these substituents are present, they may be the same or different. If the heterocyclic group is a 1H-pyrazolo[3,2-c]-S-triazole-3-yl compound, a bis type 1H-pyrazolo[3,2-c]-S-triazole compound is formed and this is of course a magenta coupler included within the scope of the present invention.

Examples of the leaving group other than hydrogen that may be bonded to the 7-position coupling site include halogens and organic groups that are bonded to the coupling site by an oxygen, nitrogen or sulfur atom. Illustrative leaving groups that are bonded to the coupling site by an oxygen atom include alkoxy, aryloxy, acyloxy and heterocyclic oxy; exemplary leaving groups that are bonded to the coupling site by a nitrogen atom include acylamino, diacylamino, sulfonamido, and 5- or 6-membered heterocyclic groups containing that nitrogen atom; and illustrative leaving groups that are bonded to the coupling site by a sulfur atom include thiocyano, alkylthio, arylthio, heterocyclic thio, arylsulfonyl and alkylsulfonyl.

Compounds preferred for the purposes of the present invention are represented by the following formula:

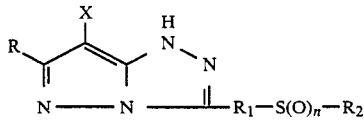

wherein $R_1$, $R_2$ and n are already defined above; X is a leaving group which leaves upon reaction with the oxidation product of a color developing agent and is also defined above.

The symbol R in the above formula represents an alkyl group, a cycloalkyl group, an aryl group or a heterocyclic group. The alkyl group may be a primary alkyl or a branched secondary or tertiary alkyl. The alkyl may have a substituent as illustrated in connection with the definition of $R_2$. If the alkyl as R is a secondary alkyl, it may preferably have the following formula:

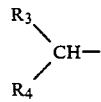

wherein $R_3$ and $R_4$ are each a halogen atom, a cyano group, a nitro group, an alkyl group, an aryl group, a heterocyclic group, or an alkyl, aryl or heterocyclic group that is bonded by an oxygen, nitrogen or sulfur atom, or an alkyl, aryl or heterocyclic group that is bonded by an acylamino, carbamoyl, sulfonamido, sulfamoyl, carbonyl, carbonyloxy, oxycarbonyl, ureido, thioureido, thioamido, sulfon or sulfonyloxy; $R_3$ and $R_4$ may combine together to form a carbon ring or a hetero ring.

Further description of $R_3$ and $R_4$ is given below. Examples of the halogen atom represented by $R_3$ or $R_4$ include Cl, Br and F. Examples of the alkyl group represented by $R_3$ or $R_4$ include straight-chained or branched alkyl groups having 1 to 20 carbon atoms (e.g. methyl, ethyl, propyl, i-propyl, sec-butyl, n-butyl, t-butyl, n-octyl, t-octyl, dodecyl and octadecyl). These groups may have substituents such as halogen atom, nitro, cyano, alkoxy, aryloxy, amino, acylamino, carbamoyl, sulfonamido, sulfamoyl, imido, alkylthio, arylthio, aryl, alkoxycarbonyl and acyl. Exemplary substituted alkyl groups include chloromethyl, bromomethyl, trichloromethyl, $\beta$-nitroethyl, $\delta$-cyanobutyl, methoxymethyl, ethoxyethyl, phenoxyethyl, N-methylaminoethyl, dimethylaminobutyl, acetaminoethyl, benzoylamino, propyl, ethylcarbamoylethyl, methanesulfonamidoethyl, ethylthioethyl, p-methoxyphenylthiomethyl, p-chlorophenylmethyl, naphthylethyl, ethoxycarbonylethyl and acetylethyl.

Examples of the aryl group as $R_3$ or $R_4$ include phenyl and naphthyl, which may have substituents as listed in connection with the description of the alkyl group.

Illustrative heterocyclic groups as $R_3$ or $R_4$ are 5- or 6-membered rings having at least one of nitrogen, oxygen and sulfur atoms and they may be aromatic or non-aromatic. Specific examples of the heterocyclic group include pyridyl, quinolyl, pyrrolyl, morpholyl, furanyl, tetrahydrofuranyl, pyrazolyl, triazolyl, tetrazolyl, thiazolyl, oxazolyl, imidazolyl and thiadiazolyl. These heterocyclic groups may have substituents as listed in connection with the description of the alkyl group.

Examples of the carbon ring formed by combination of $R_3$ and $R_4$ include cyclopropyl, cyclopentyl, cyclohexyl and cyclohexenyl. Examples of the hetero ring that may be formed by $R_3$ as combined with $R_4$ include piperidyl, pyrrolidyl, dioxanyl and morpholinyl.

Preferred aryl groups as R are substituted and unsubstituted phenyl groups. Specific examples of the heterocyclic group as R are furan ring and thiophene ring.

When $R_2$ is an alkyl group or a cycloalkyl group, $R_1$ is an alkylene group, which preferably has 3 to 6 carbon atoms in the straight chain.

The 1H-pyrazolo[3,2-c]-S-triazole derived magenta couplers in accordance with the present invention are illustrated by, but by no means limited to, the following compounds. Preferably, these couplers are non-diffusible and have molecular weights not exceeding 450.

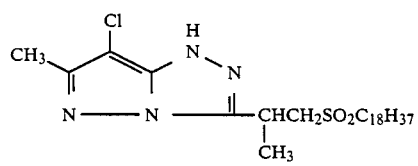

(1)

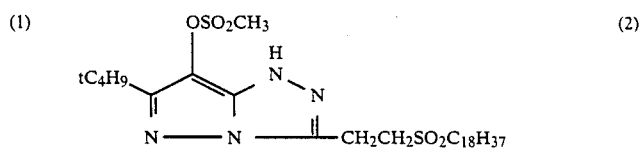

(2)

-continued
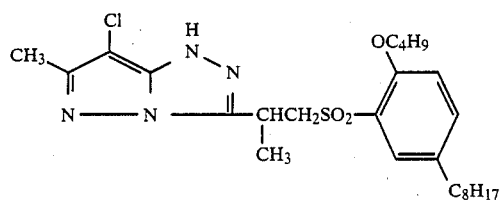 (3)
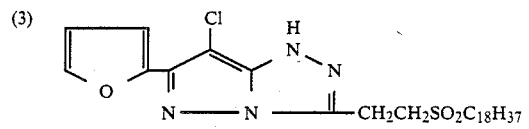 (4)
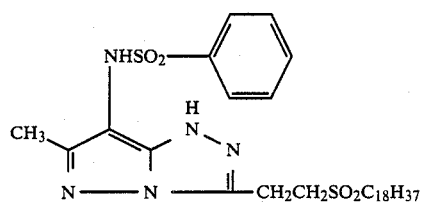 (5)
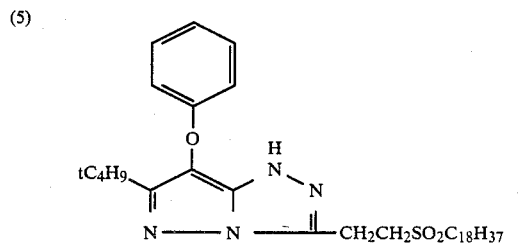 (6)
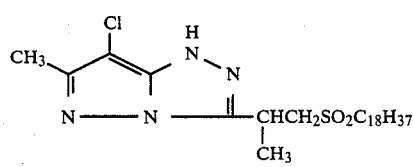 (7)
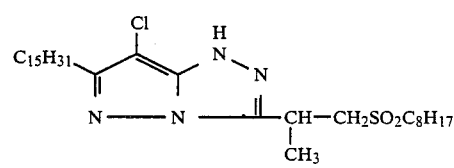 (8)
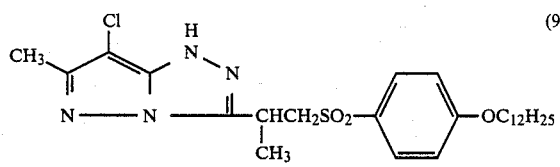 (9)
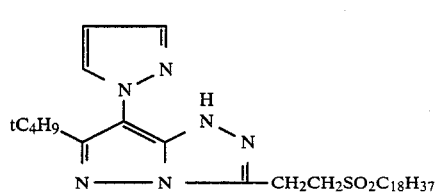 (10)
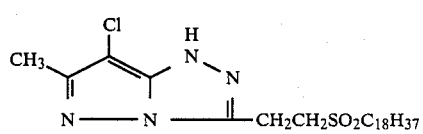 (11)
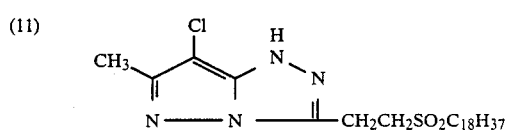 (12)
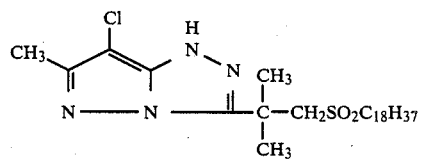 (13)
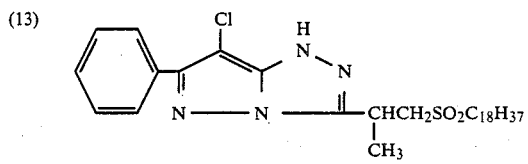 (14)
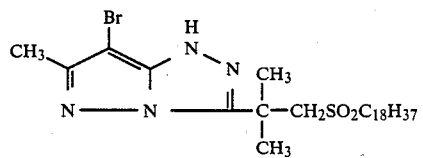 (15)
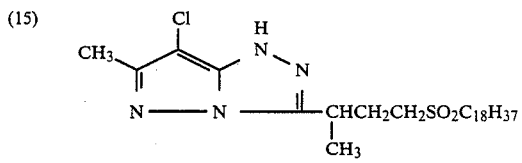 (16)
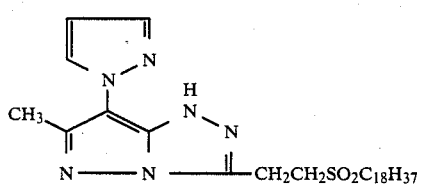 (17)
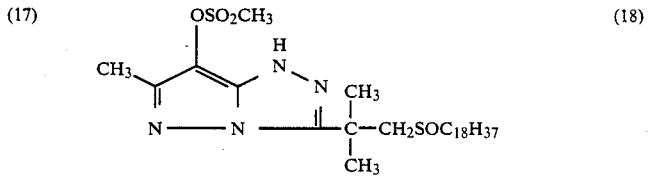 (18)

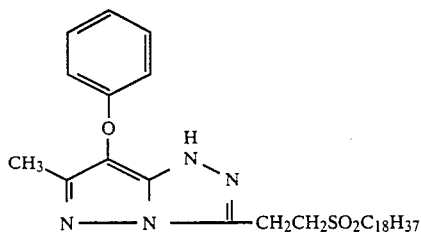
(19)
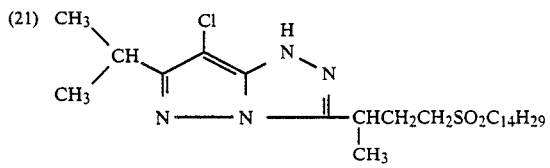
(20)
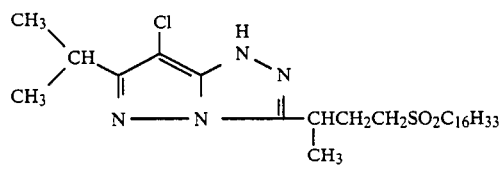
(21)
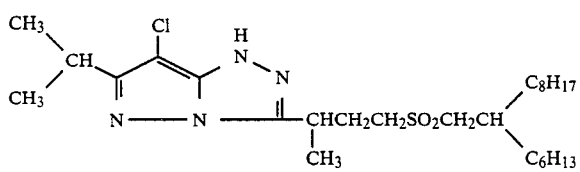
(22)
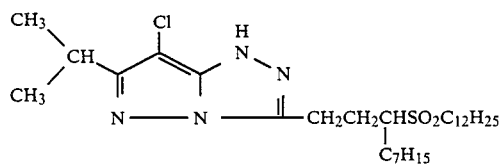
(23)
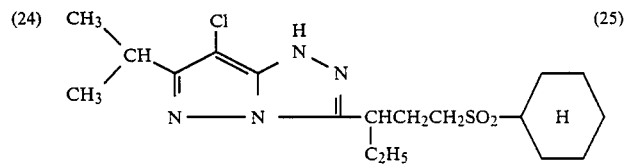
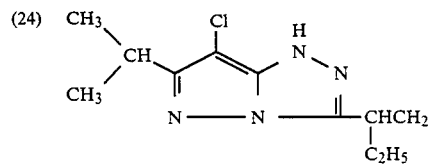
(24)
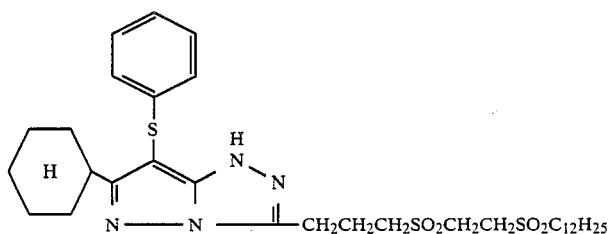
(25)
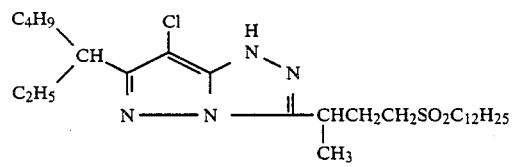
(26)
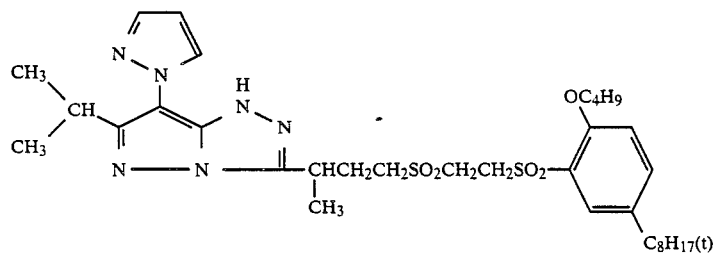
(27)
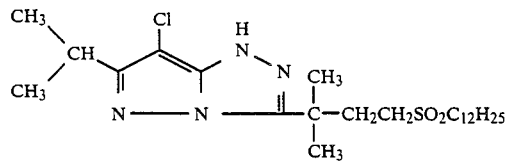
(28)
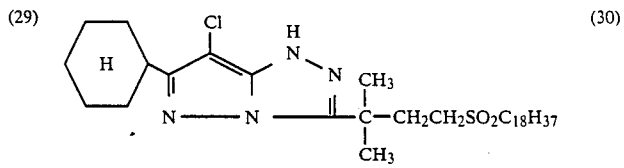
(29)
(30)

-continued
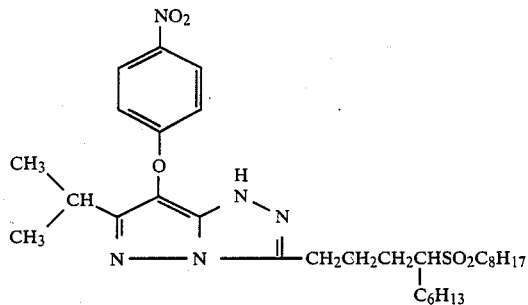 (31)
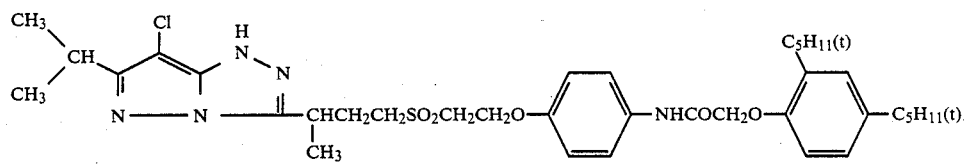 (32)
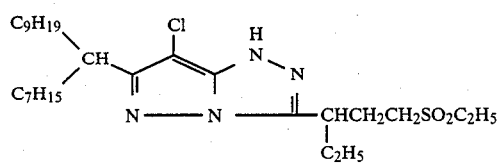 (33)
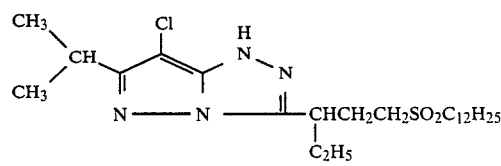 (34)
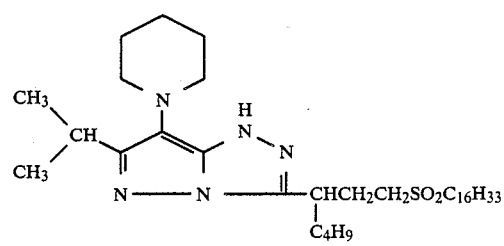 (35)
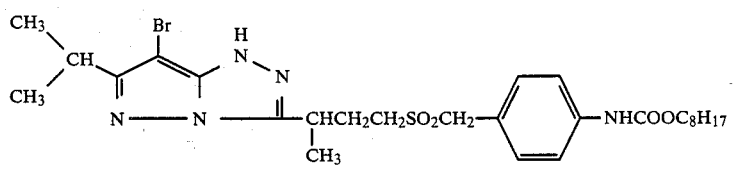 (36)
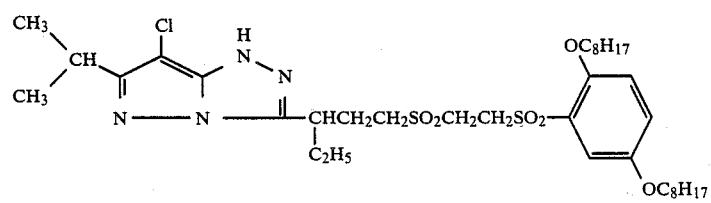 (37)
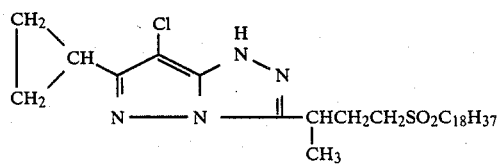 (38)
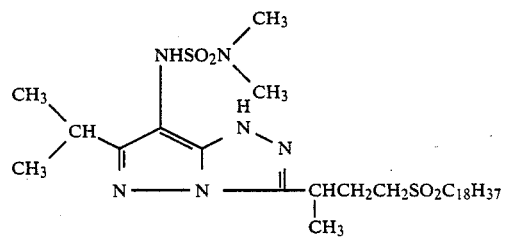 (39)

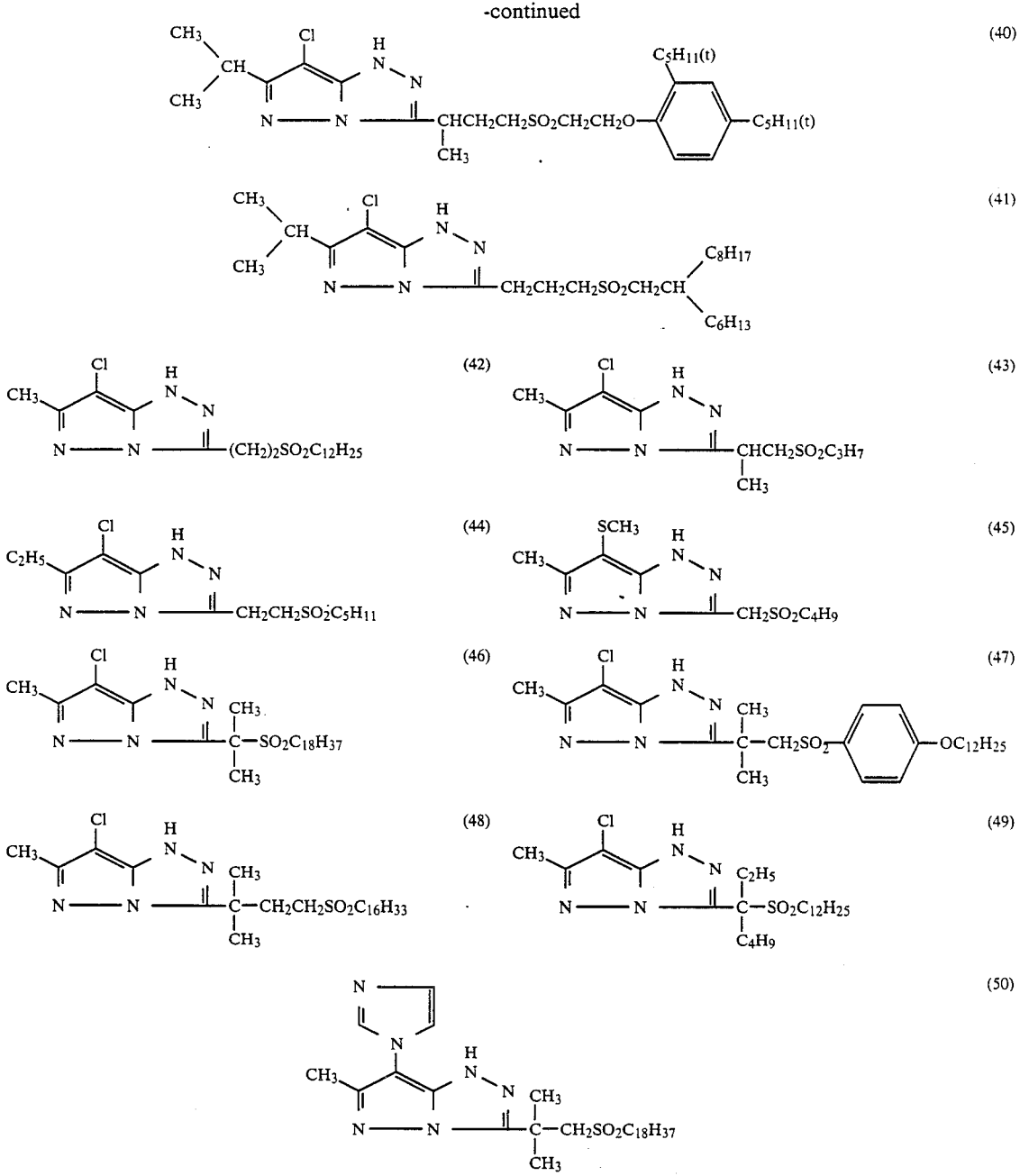

The synthesis of 1H-pyrazolo[3,2-c]-S-triazole after the introduction of $R_2$—$S(O)_n$—$R_1$—COOH may be performed by reference to Research Disclosure No. 12443 and Journal of the Chemical Society, Ferkin I, 1977, pp. 2047–2052. The introduction of a leaving group at the 7-position coupling site may be performed by reference to U.S. Pat. No. 3,725,067 and Unexamined Published Japanese Patent Application No. 99437/1984.

The group $R_2$—$SO_2$—$R_1$-COOH is obtained by oxidizing the corresponding $R_2$—S—$R_1$-COOH with hydrogen peroxide in accordance with the method described in Unexamined Japanese Patent Application No. 24321/1972. The group $R_2$—SO—$R_1$—COOH is obtained by reacting equimolar amounts of $R_2$—S—$R_1$—COOH and hydrogen peroxide under cooling.

Synthesis of Magenta Coupler (1)

The reaction scheme is shown below:

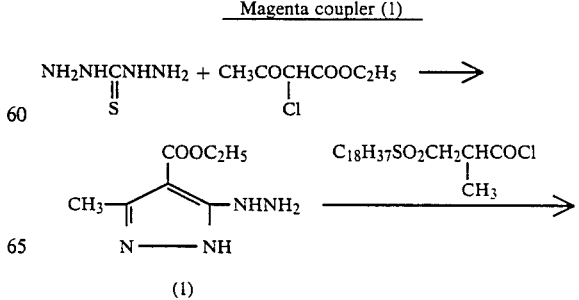

Magenta coupler (1)

-continued
Magenta coupler (1)

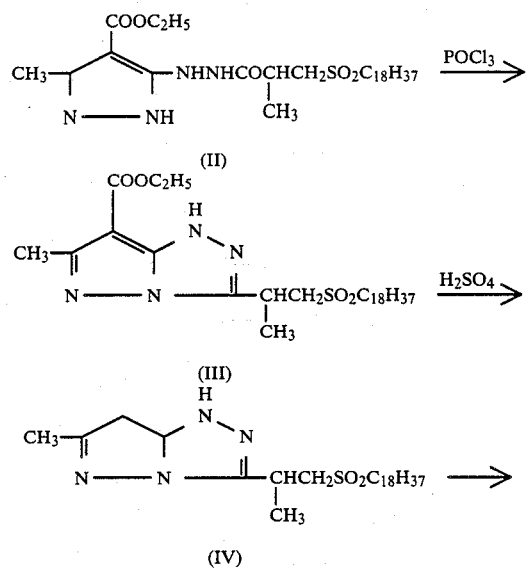

(1) Synthesis Compound (I)

This compound was prepared by the method described in Journal of the Chemical Society, Perkin I, 1977, pp. 2047-2052.

(2) Synthesis of Compound (II)

Ninety-two grams of (I) was dispersed in 1,000 ml of acetonitrile. To the dispersion, 60 g of triethylamine was added and acid chloride prepared by reacting 222 g of acid with thionyl chloride was added dropwise to the mixture under refluxing. The resulting mixture was refluxed for an additional 30 minutes. After cooling the mixture, the crystal was recovered by filtration, washed with water thoroughly and dried. The end compound was obtained in a yield of 80%.

(3) Synthesis of Compound (III)

To 1,500 ml of toluene, 193 g of (II) and 53.5 g of phosphorus oxychloride were added and the mixture was refluxed for 5 hours. Thereafter, the toluene was distilled off and 1,500 ml of acetonitrile and 80 g of pyridine were added to the residue and the resulting mixture was refluxed for an additional 1.5 hours. After distilling off the acetonitrile, water was added to the residue and the resultant crystal was recovered by filtration. The crystal was washed with water, dried and recrystallized from acetonitrile to give the end compound (III).

(4) Synthesis of Compound (IV)

One hundred and thirty grams of (III) was added to a mixture of glacial acetic acid (1,000 ml), concentrated sulfuric acid (100 ml) and water (20 ml) and the resultant mixture was refluxed for 10 hours. After leaving the mixture to cool down, an aqueous caustic soda solution consisting of 1,000 ml of water and 180 g of caustic soda was added under agitation. The resulting crystal was recovered by filtration, washed thoroughly with water, and dried to give the end compound (IV).

(5) Synthesis of Compound (1)

Twenty grams of (IV) was dissolved in chloroform, and to the solution, an equivalent amount of N-chlorosuccinimide was added. The mixture was held at room temperature for 1 hour to perform reaction. The reaction mixture was washed with dilute alkali and subjected to further washing with water. The chloroform was distilled off and the residue was purified by column chromatography on silica gel using benzene-acetone as a solvent. The purified residue was identified as the end compound by NMR spectrum and mass spectrum.

Synthesis of Magenta Coupler (47)

The synthesis scheme is shown below:

magenta coupler (47)

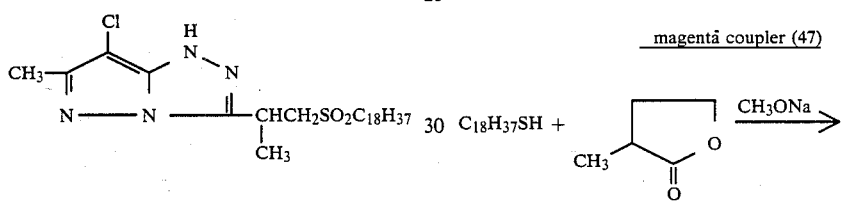

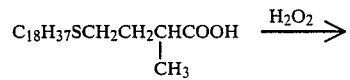

A

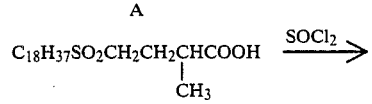

B

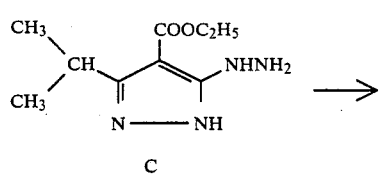

C

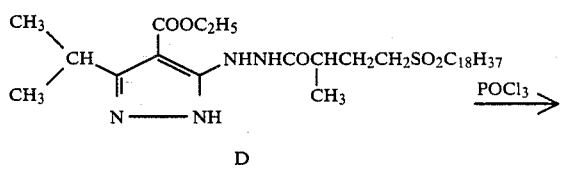

D

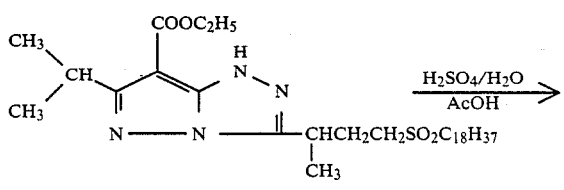

E

-continued
magenta coupler (47)

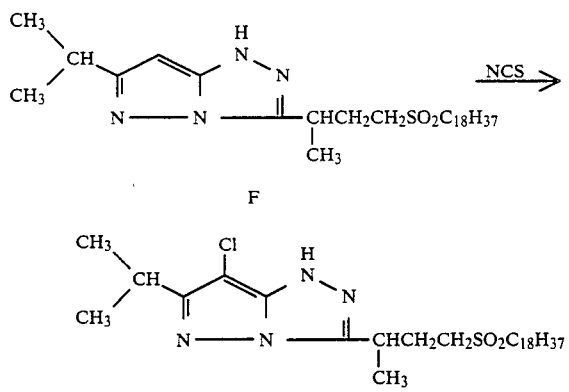

(1) Synthesis of Compound A

A mixture of octadecylcaptan (28.6 g) and α-methyl-γ-butyrolactone (10 g) was dissolved in dimethylformamide (200 ml), and after addition of 28% aqueous sodium methylate (19.3 g), the mixture was heated at 80° C. for 2 hours under agitation. After the reaction, the mixture was poured into water and rendered acidic with hydrochloric acid.

The resulting crystal was recovered by filtration and washed with methanol to provide 38.6 g of compound A. This was used in the subsequent step of reaction without purification.

(2) Synthesis of Compound B

Compound A (38.6 g) was dissolved in acetic acid (200 ml) and to the solution, 25.4 g of 35% $H_2O_2$ was slowly added dropwise at 60°-70° C. After the reaction, the mixture was cooled and the resulting crystal was recovered by filtration. After washing with 80% methanol, the crystal was recrystallized from methanol to obtain 26 g of compound B. m.p. 109°-110° C.

(3) Synthesis of Compound D

In 200 ml of acetonitrile, 11.4 g of hydrazine compound (compound C) was dissolved and, to the solution, 6.1 g of triethylamine was added and the mixture was boiled under agitation. Acid chloride prepared from 25.8 g of the acid obtained in (2) was dissolved in a small amount of acetonitrile and the solution was added dropwise to the stirred solution.

Thereafter, the mixture was refluxed for 1 hour and cooled to cause crystallization. The crystal was recovered by filtration and washed with water. After drying, the crystal was recrystallized from methanol to obtain 27.6 g of compound D. m.p. 125°-127° C.

(4) Synthesis of Compound E

Compound D (24.5 g) was dissolved in 150 ml of toluene and, to the solution, 6.2 g of phosphorus oxychloride was added and the resulting mixture was refluxed for 3 hours. Thereafter, the mixture was cooled to room temperature, and stirred for 10 minutes after addition of triethylamine (12 g). The stirred mixture was washed with warm water and the toluene was distilled off under vacuum. The residue was purified by column chromatography and recrystallized from methanol to obtain 15.0 g of compound E. m.p. 78°-81° C.

(5) Synthesis of Compound F

Compound E (15.0 g) was added to a mixture of concentrated sulfuric acid (15 ml), glacial acetic acid (75 ml) and water (15 ml) and the resultant mixture was refluxed for 8 hours. After the reaction, the mixture was poured into iced water having 30 g of sodium hydroxide dissolved therein. The crystal was recovered by filtration and, after thorough washing with water, recrystallized from methanol to provide 10.2 g of compound F. m.p. 98°-100° C.

(6) Synthesis of Magenta Coupler (47)

Compound F (10.0 g) was dissolved in 100 ml of chloroform and, to the solution, 2.6 g of N-chlorosuccinimide was added and the mixture was held at room temperature for 30 minutes. Thereafter, the reaction mixture was washed with water and the chloroform was distilled off. The residue was mixed with hexane and heated to cause crystallization. The crystal was recovered by filtration and recrystallized from methanol to provide 6.8 g of the end compound. m.p. 57°-59° C.

Synthesis of Magenta Couplers (2), (6) and (10)

The 1H-pyrazolo[3,2-c]-S-triazole nucleus was prepared in accordance with Research Disclosure No. 12443, and respective leaving groups were introduced by the procedures described in U.S. Pat. No. 3,725,067 and Unexamined Published Japanese Patent Application No. 99437/1984.

The 1H-pyrazolo[3,2-c]-S-triazole nucleus in other magenta couplers was prepared as in the case of the synthesis of magenta coupler (1). Leaving groups were introduced in magenta couplers (5), (15), (17), (18) and (19) by referring to the disclosure in U.S. Pat. No. 3,725,067 and Unexamined Published Japanese Patent Application No. 99437/1984.

The silver halide color photographic material of the present invention may contain conventional dye forming couplers.

Known open-chain ketomethylene couplers may be used as yellow-forming couplers. Benzoylacetanilide and pivaloylacetanilide compounds are particularly useful. Specific examples of the usable yellow forming couplers are described in U.S. Pat. Nos. 2,875,057, 3,265,506, 3,408,194, 3,551,155, 3,582,322, 3,725,072, and 3,891,445; German Pat. No. 1,547,868, German Patent Application (OLS) Nos. 2,219,917, 2,261,361 and 2,414,006; British Pat. No. 1,425,020; Japanese Patent Publication No. 10783/1976, Unexamined Published Japanese Patent Application Nos. 26133/1972, 73147/1983, 102036/1976, 6341/1975, 123342/1975, 130442/1975, 21827/1976, 87650/1975, 82424/1977 and 115219/1977.

Usable cyan forming couplers are phenolic and naphtholic compounds. Specific examples are found in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929; German Patent Application (OLS) Nos. 2,414,830 and 2,454,329; and Unexamined Published Japanese Patent Application Nos. 59838/1973, 26034/1976, 5055/1973, 146828/1976, 69624/1977 and 90932/1977.

As magenta forming couplers, one or more of the couplers prepared in accordance with the present invention may be used. They may also be used in combination with known magenta couplers such as pyrazolone compounds, indazolone compounds, cyanoacetyl compounds, pyrazolinobenzimidazole compounds and pyrazolotriazole compounds. It should however be emphasized that at least one of the magenta couplers incorporated in the silver halide color photographic material of the present invention must be the coupler defined in accordance with the invention.

The coupler of the present invention may also be used in combination with colored couplers capable of color correction, or development inhibitor releasing couplers (DIR couplers) that are effective for producing improved image quality.

The magenta coupler of the present invention and the respective couplers associated thereto may be introduced into silver halide emulsion layers by any known method such as one described in U.S. Pat. No. 2,322,027. For example, the couplers are dispersed in hydrophilic colloids after being dissolved in high-boiling organic solvents or low-boiling organic solvents. Examples of the former type include alkyl esters of phthalic acid (e.g., dibutyl phthalate and dioctyl phthalate), phosphate esters (e.g., diphenyl phosphate, triphenyl phosphate, tricresyl phosphate and dioctylbutyl phosphate), citrate esters (e.g., tributyl acetylcitrate), benzoate esters (e.g., octyl benzoate), alkylamides (e.g., diethyl laurylamide), aliphatic acid esters (e.g. dibutoxyethyl succinate and dioctyl azelate) and trimesic acid esters (e.g. tributyl trimesate). The low-boiling organic solvents are those which boil at between about 30° C. and 150° C., and examples are lower alkyl acetates (e.g. ethyl acetate and butyl acetate), ethyl propionate, secondary butyl alcohol, methyl isobutyl ketone, $\beta$-ethoxyethyl acetate and methyl cellosolve acetate. The high-boiling organic solvents may be used in combination with the low-boiling organic solvents.

Dispersion methods using polymers may also be used and such methods are described in Japanese Patent Publication No. 39853/1976 and Unexamined Published Japanese Patent Application No. 59943/1976.

The magenta coupler of the present invention is incorporated in a silver halide emulsion layer usually in the amount of from 0.005 to 2 moles, preferably from 0.03 to 0.5 mole, per mole of silver halide.

The magenta coupler of the present invention forms a satisfactorily light-fast dye image, but even higher light fastness may be obtained by using an anti-fading agent or by overlaying the emulsion layer of interest with a layer containing an ultraviolet absorber.

Illustrative anti-fading agents include hydroquinone derivatives of the type described in U.S. Pat. Nos. 2,360,290, 2,418,613, 2,673,314, 2,701,197, 2,704,713, 2,728,659, 2,732,300, 2,735,765, 2,710,801 and 2,816,028, as well as British Pat. No. 1,363,921; gallic acid derivatives as described in U.S. Pat. Nos. 3,457,079 and 3,069,262; p-alkoxyphenols of the type described in U.S. Pat. Nos. 2,735,765 and 3,698,909, as well as Japanese Patent Publication No. 20977/1974 and 6623/1977; p-oxyphenol derivatives of the type described in U.S. Pat. Nos. 3,432,300, 3,573,050, 3,574,627 and 3,764,337, as well as Unexamined Published Japanese Patent Application Nos. 35633/1977, 147434/1977 and 152225/1977; and bisphenols as described in U.S. Pat. No. 3,700,455.

Exemplary ultraviolet absorbers include aryl-substituted benzotriazole compounds as described in U.S. Pat. No. 3,533,794, 4-thiazolidone compounds (as described in U.S. Pat. Nos. 3,314,794 and 3,352,681), benzophenone compounds (as described in Unexamined Published Japanese Patent Application No. 2784/1971), connamic acid ester compounds (as described in U.S. Pat. Nos. 3,705,805 and 3,707,375), butadiene compounds (as described in U.S. Pat. No. 4,045,229), and benzoxidole compounds (as described in U.S. Pat. No. 3,700,455). Other compounds usable as UV absorbers are found in U.S. Pat. No. 3,499,762 and Unexamined Published Japanese Patent Application No. 48535/1979.

Any of the silver halides that are incorporated in conventional silver halide emulsions may be used in the present invention and they include silver bromide, silver chloride, silver iodobromide, silver chlorobromide and silver chloroiodobromide. In order to provide sensitivity for the desired spectral wavelength region, the silver halides used in the present invention may be spectrally sensitized by suitable selected sensitizing dyes. Usable dyes include cyanine, merocyanine, complex cyanine, complex merocyanine, holopolar cyanine, hemicyanine, styryl and hemioxonole dyes.

Useful sensitizing dyes are described in, for example, German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572; British Pat. No. 1,242,588; and Japanese Patent Publication Nos. 14030/1969 and 24844/1977.

These sensitizing dyes may be used either individually or in combination. Combined sensitizing dyes are often used for the purpose of supersensitization, as typically described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707; British Pat. Nos. 1,344,281 and 1,507,803; Japanese Patent Publication Nos. 4936/1968 and 12375/1978; and Unexamined Published Japanese Patent Application Nos. 110618/1977 and 109925/1977.

The silver halide emulsion used in the present invention may incorporate a variety of known photographic additives such as those described in Research Disclosure No. 17643.

The silver halide color photographic material of the present invention may use any support material that is properly selected from among known materials depending on the specific object, such as plastic films, plastic laminated paper, baryta paper and synthetic paper.

The silver halide color photographic material of the invention may adopt any of the layer arrangements commonly used in the photographic industry.

The so arranged silver halide color photographic material of the invention is exposed and thereafter subjected to color development by a variety of photographic processing techniques. The color developer used to process this photographic material may contain any of the known aromatic primary amine color developing agents that are extensively used in various color photographic processes. Such developing agents include aminophenolic and p-phenylenediamine derivatives. These compounds are generally used in salt forms, such as hydrochlorides or sulfates, which are stabler than the free state. These compounds are used in concentrations that generally range from about 0.1 to about 30 g, preferably from about 1 g to about 1.5 g, per liter of the color developer.

Illustrative aminophenolic developing agents include o-aminophenol, p-aminophenol, 5-amino-2-oxytoluene, 2-amino-3-oxytoluene, and 2-oxy-3-amino-1,4-dimethylbenzene.

Particularly useful primary aromatic amino color developing agents are N,N'-dialkyl-p-phenylenediamine compounds wherein the alkyl or phenyl group may have a suitable substituent. Among these compounds, the following are particularly advantageous: N,N'-diethyl-p-phenylene-diamine hydrochloride, N-methyl-p-phenylenediamine hydrochloride, N,N'-dimethyl-p-phenylenediamine hydrochloride, 2-amino-5-(N-ethyl-N-dodecylamino)-toluene, N-ethyl-N-β-methanesulfonamidoethyl-3-methyl-4-aminoaniline sulfate, N-ethyl-N-β-hydroxyethylaminoaniline, 4-amino-3-methyl-N,N'-diethylaniline, and 4-amino-N-(2-methoxyethyl)-N-ethyl-3-methylaniline-p-toluene sulfonate.

In addition to these primary aromatic amino color developing agents, the color developer used in the processing of the photographic material of the present invention may contain a variety of additives that are commonly incorporated in color developers and such additives include alkali agents (e.g. sodium hydroxide, sodium carbonate and potassium carbonate), alkali metal sulfites, alkali metal bisulfites, alkali metal thiocyanates, alkali metal halides, benzyl alcohol, water softeners and thickeners. The pH of the color developer is usually at least 7 and most generally ranges from about 10 to about 13.

After color development, the photographic material of the present invention is processed by a solution having the fixing ability. If this solution is a fixing bath, its use is preceded by a bleaching step. The bleaching bath used in the bleaching step or the bleaching agent used in a bleach-fixing bath is made of a metal complex salt of an organic acid. This metal complex salt has the ability not only to oxidize metallic silver (i.e., formed as a result of development) into silver halide but also to ensure complete color formation by a color former. The structure of this metal complex salt is such that an organic acid such as an aminopolycarboxylic acid, oxalic acid or citric acid is coordinated to a metal ion such as iron, cobalt or copper. The organic acids most preferred for use in forming metal complex salts are polycarboxylic acids or aminopolycarboxylic acids. The polycarboxylic acids or aminopolycarboxylic acids may be in the form of alkali metal salts, ammonium salts or water-soluble salts.

Typical examples of polycarboxylic acids or aminopolycarboxylic acids are listed below:
(1) ethylenediaminetetraacetic acid;
(2) diethylenetriaminepentaacetic acid;
(3) ethylenediamine-N-(β-oxyethyl)-N,N',N'-triacetic acid;
(4) propylenediaminetetraacetic acid;
(5) nitrilotriacetic acid;
(6) cyclohexanediaminetetraacetic acid;
(7) iminodiacetic acid;
(8) dihydroxyethylglycincitric acid (or tartaric acid);
(9) ethyletherdiaminetetraacetic acid;
(10) glycoletherdiaminetetraacetic acid;
(11) ethylenediaminetetrapropionic acid;
(12) phenylenediaminetetraacetic acid;
(13) ethylenediaminetetraacetic acid disodium salt;
(14) ethylenediaminetetraacetic acid tetra (trimethylammonium) salt;
(15) ethylenediaminetetraacetic acid tetrasodium salt;
(16) diethylenetriaminepentaacetic acid pentasodium salt;
(17) ethylenediamine-N-(β-oxyethyl)-N,N',N'-triacetic acid sodium salt;
(18) propylenediaminetetraacetic acid sodium salt;
(19) nitrilotriacetic acid sodium salt; and
(20) cyclohexanediaminetetraacetic acid sodium salt.

In addition to metal complex salts of these organic acids which are used as bleaching agents, the bleaching bath used in processing the color photographic material of the present invention may contain a variety of additives, and preferred additives are rehalogenating agents such as alkali or ammonium halides (e.g. potassium bromide, sodium bromide, sodium chloride and ammonium bromide), metal salts and chelating agents. Any other additives that are conventionally incorporated in bleaching baths may also be used and they include pH buffers (e.g. borate, oxalate, acetate, carbonate and phosphate salts), alkylamines and polyethylene oxides.

The fixing bath and bleach-fixing bath may also contain one or more pH buffers that are selected from among sulfites (e.g. ammonium sulfite, potassium sulfite, ammonium bisulfite, potassium bisulfite, sodium bisulfite, ammonium metabisulfite, potassium metabisulfite, and sodium metabisulfite), and a variety of acids or salts (e.g. boric acid, borax, sodium hydroxide, potassium hydroxide, sodium carbonate, potassium carbonate, sodium bicarbonate, potassium bicarbonate, acetic acid, sodium acetate and ammonium hydroxide).

If the photographic material of the present invention is processed in a bleach-fixing bath as it is supplied with a blix replenisher, thiosulfates, thiocyanates, sulfites or other salts may be incorporated either in the bleach-fixing bath or in the replenisher that is fed to said blix bath.

In order to increase the activity of the bleach-fixing bath used in processing the photographic material of the present invention, air or oxygen may be blown into a tank containing the bleach-fixing bath or its replenisher. Alternatively, a suitable oxidant such as hydrogen peroxide, bromate or persulfate may be added into the tank.

The following examples are provided for further illustration of the claimed photographic material but are not to be construed as limiting the invention.

EXAMPLE 1

One tenth of a mole, per mole of silver, of one of the magenta couplers listed in Table 1 (which follows) was mixed with an equal weight of tricresyl phosphate and three times the coupler's weight of ethyl acetate, and the mixture was heated to 60° C. to form a complete solution. The solution was then mixed with 1,200 ml of 5% aqueous gelatin solution containing 120 ml of a 5% aqueous solution of Alkanol B (trade name of du Pont for alkylnaphthalene sulfonate). The mixture was emulsified with an ultrasonic disperser and the dispersion obtained was added to 4 kg of a green-sensitive silver iodobromide emulsion (containing 6 mol% AgI). To the mixture, 120 ml of a 2% solution (water: methanol = 1:1) of 1,2-bis-(vinylsulfonyl)ethane was added as a hardener, and the so prepared coating solution was applied to a subbed transparent polyester base, and the web was dried to provide a sample of color photographic material (with silver deposit of 20 mg/100 cm$^2$). The other samples were prepared by the same procedure.

Each of the samples thus prepared was subjected to exposure through an optical wedge as in the conventional process and subsequently processed by the following scheme. The results of such photographic processing are shown in Table 1 below.

| Steps | Processing scheme | |
|---|---|---|
| | Temperature, °C. | Time |
| Color development | 38 | 3 min, 15 sec |

-continued

| Steps | Processing scheme Temperature, °C. | Time |
|---|---|---|
| Bleaching | 38 | 4 min, 20 sec |
| Washing | 38 | 3 min, 15 sec |
| Fixing | 38 | 4 min, 20 sec |
| Washing | 38 | 3 min, 15 sec |
| Stabilizing | 38 | 1 min, 30 sec |
| Drying | 47 to 55 | 16 min, 30 sec |

The formulation of each of the processing solutions used is indicated below.

| Color developer | |
|---|---|
| Potassium carbonate | 30 g |
| Sodium hydrogencarbonate | 2.5 g |
| Potassium sulfite | 5 g |
| Sodium bromide | 1.3 g |
| Potassium iodide | 2 mg |
| Hydroxylamine sulfate | 2.5 g |
| Sodium chloride | 0.6 g |
| Diethylenetriaminepentaacetic acid sodium salt | 2.5 g |
| 4-amino-3-methyl-N—ethyl-N—(β-hydroxyethyl)aniline sulfate | 4.8 g |
| Potassium hydroxide | 1.2 g |
| Water to make | 1,000 ml |
| pH adjusted to 10.06 by addition of potassium hydroxide or 20% $H_2SO_4$. | |
| Bleaching bath | |
| Ethylenediaminetetraacetic acid iron ammonium salt | 100 g |
| Ethylenediaminetetraacetic acid | 10 g |
| Ammonium bromide | 150 g |
| Glacial acetic acid | 40 ml |
| Sodium bromate | 10 g |
| Water to make | 1,000 ml |
| pH adjusted to 3.5 by addition of ammonia water or glacial acetic acid. | |
| Fixing bath | |
| Ammonium thiosulfate | 180 g |
| Anhydrous sodium sulfite | 12 g |
| Sodium metabisulfite | 2.5 g |
| Ethylenediaminetetraacetic acid disodium salt | 0.5 g |
| Sodium carbonate | 10 g |
| Water to make | 1,000 ml |
| Stabilizing bath | |
| Formalin (37% aq. sol.) | 2 ml |
| Konidax (product of Konishiroku Photo Industry Co., Ltd.) | 5 ml |
| Water to make | 1,000 ml |

TABLE 1

| Sample No. | Coupler used | Specific sensitivity[1] | Maximum density | Formalin resistance[2] | Light fastness[3] |
|---|---|---|---|---|---|
| 1-11 | Comparative coupler 1 | 100 | 2.64 | 92 | 25 |
| 1-12 | Comparative coupler 2 | 96 | 2.58 | 91 | 27 |
| 1-13 | Comparative coupler 3 | 103 | 2.70 | 93 | 23 |
| 1-14 | Comparative coupler 4 | 102 | 2.71 | 94 | 24 |
| 1-15 | Coupler (11) of the invention | 100 | 2.63 | 90 | 35 |
| 1-16 | Coupler (12) of the invention | 101 | 2.65 | 92 | 34 |
| 1-17 | Coupler (1) of the invention | 99 | 2.58 | 93 | 39 |
| 1-18 | Coupler (7) of the invention | 102 | 2.75 | 91 | 40 |
| 1-19 | Coupler (3) of the invention | 105 | 2.81 | 93 | 37 |
| 1-20 | Coupler (4) of the invention | 110 | 2.92 | 90 | 35 |
| 1-21 | Coupler (19) of the invention | 108 | 2.90 | 92 | 33 | acl Notes (1) The specific sensitivity is expressed as the reciprocal of the exposure that provides a fog plus 0.1 density, with the value for sample No. 11 (using comparative coupler 1) being taken as 100.

(2) A sample was subjected to color development after it was held for 3 days in a sealed container of 0.9% aqueous formalin (6 ml) conditioned at 30° C. and 62% r.h. An untreated sample was also color developed. The formalin resistance of the first sample was calculated by the following formula:

$$\text{Formalin resistance} = \frac{\text{Color density of the treated sample}}{\text{Color density of the untreated sample}} \times 100 \, (\%)$$

(3) A color-developed sample was illuminated in a xenon fadeometer for 5 days and the percentage residual dye for the initial density (D) of 1.0 was calculated to determine the lightfastness of the image:

$$\text{Light fastness} = \frac{\text{Density after 5-day illumination in xenon fadeometer}}{1.0} \times 100 \, (\%)$$

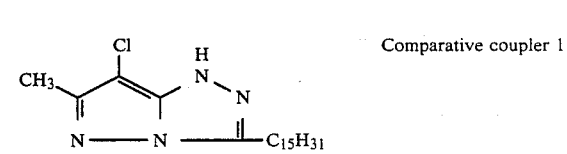

Comparative coupler 1

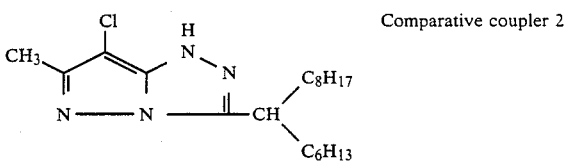

Comparative coupler 2

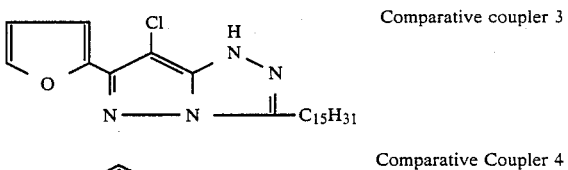

Comparative coupler 3

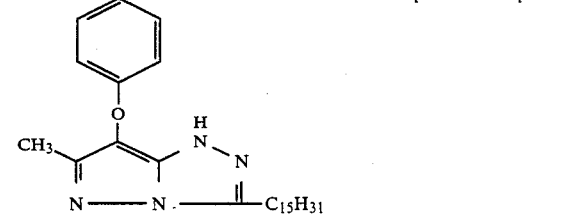

Comparative Coupler 4

The data in Table 1 show that the couplers prepared in accordance with the present invention were improved over the comparative couplers in terms of color formation and the production of formalin-resistant and light-fast dye images.

EXAMPLE 2

Sample Nos. 1-11 to 1-19 prepared in Example 1 were exposed through an optical wedge and subsequently processed by the following scheme. The results are shown in Table 2. The specific sensitivity and light fastness were measured by the same methods as used in Example 1.

| Processing scheme: | | |
|---|---|---|
| Color development | 38° C. | 3 min., 30 sec |
| Bleach-fixing | 33° C. | 1 min., 30 sec |
| Stabilizing or washing | 25-30° C. | 3 min. |
| Drying | 75-80° C. | ca. 2 min. |

The solutions used in this scheme had the following formulations.

| Color developer | |
|---|---|
| Benzyl alcohol | 15 ml |
| Ethylene glycol | 15 ml |
| Potassium sulfite | 2.0 g |
| Potassium bromide | 0.7 g |
| Sodium chloride | 0.2 g |
| Potassium carbonate | 30.0 g |
| Hydroxylamine sulfate | 3.0 g |
| Tripolyphosphoric acid (TPPS) | 2.5 g |
| 3-Methyl-4-amino-N—ethyl-N—(β-methane-sulfonamidoethyl)aniline sulfate | 5.5 g |
| Brightener (4,4'-diaminostilbenzosulfonic acid derivative) | 1.0 g |
| Potassium hydroxide | 2.0 g |
| Water to make | 1,000 ml |
| pH adjusted to 10.20 | |
| Bleachi-fixing bath | |
| Ethylenediaminetetraacetic acid iron (III) ammonium dihydrate salt | 60 g |
| Ethylenediaminetetraacetic acid | 3 g |
| Ammonium thiosulfate (70% aq. sol.) | 100 ml |
| Ammonium sulfite (40% aq. sol.) | 27.5 ml |
| pH adjusted to 7.1 by addition of potassium carbonate or glacial acetic acid | |
| Water to make | 1,000 ml |
| Stabilizing bath | |
| 5-Chloro-2-methyl-4-isothiazolin-3-one | 1.0 g |
| Ethylene glycol | 10 g |
| 1-Hydroxyethylidene-1,1'-diphosphonic acid | 2.5 g |
| Bismuth chloride | 0.2 g |
| Magnesium chloride | 0.1 g |
| Ammonium hydroxide (28% aq. sol.) | 2.0 g |
| Sodium nitrilotriacetate | 1.0 g |
| Water to make | 1,000 ml |
| pH adjusted to 7.0 by addition of ammonium hydroxide or sulfuric acid. | |

TABLE 2

| Sample No. | Coupler used | Specific sensitivity | Maximum density | Light fastness |
|---|---|---|---|---|
| 2-11 | Comparative coupler 1 | 100 | 2.41 | 24 |
| 2-12 | Comparative coupler 2 | 100 | 2.42 | 26 |
| 2-13 | Comparative coupler 3 | 105 | 2.51 | 23 |
| 2-14 | Comparative coupler 4 | 108 | 2.52 | 25 |
| 2-15 | Coupler (11) of the invention | 101 | 2.42 | 37 |
| 2-16 | Coupler (12) of the invention | 99 | 2.39 | 38 |
| 2-17 | Coupler (1) of the invention | 77 | 2.39 | 36 |
| 2-18 | Coupler (7) of the invention | 98 | 2.38 | 40 |
| 2-19 | Coupler (3) of the invention | 102 | 2.43 | 37 |
| 2-20 | Coupler (4) of the invention | 105 | 2.50 | 38 |
| 2-21 | Coupler (19) of the invention | 104 | 2.48 | 34 |

EXAMPLE 3

A sample of silver halide color photographic material was prepared by coating the following layers in sequence on a support made of polyethylene coated paper containing anatase type $TiO_2$. The amounts of the additives incorporated in each of the layers described below are based on an area of 100 $cm^2$.

(1) Layer containing 20 mg of gelatin, 5 mg in terms of silver of a blue-sensitive silver chlorobromide emulsion, and 3 mg of dioctyl phthalate coupler solvent having dissolved the resin 8 mg of Y-coupler* and 0.1 mg of 2,5-di-t-octylhydroquinone:

(2) Interlayer containing 12 mg of gelatin, and 2 mg of dibutyl phthalate UV absorber solvent having 0.5 mg 2,5-di-t-octylhydroquinone and 4 mg of UV absorber* dissolved therein:

(3) Layer containing 18 mg of gelatin, 4 mg in terms of silver of a green-sensitive silver chlorobromide emulsion, and 2.5 mg of dioctyl phthalate coupler solvent having dissolved therein 5 mg of M-coupler*, 2 mg of antioxidant* and 0.2 mg of 2,5-di-t-octylhydroquinone:

(4) Interlayer having the same composition as (2):

(5) Layer containing 16 mg of gelatin, 4 mg in terms of silver of a red-sensitive silver chlorobromide emulsion, and 2.0 mg of tricresyl phosphate coupler solvent having dissolved therein 3.5 mg of C-coupler* and 0.1 mg of 2,5-di-t-octyl-hydroquinone:

(6) Gelatin protective layer containing 9 mg of gelatin.

Each of the layers (1) to (6) also contained a coating aid, while layers (4) to (6) further contained a gelatin crosslinking agent. The ultraviolet absorber used in each of the layers (2) and (4) was a mixture of UV-1 and UV-2 having the structures shown below. The antioxidant incorporated in layer (3) was di-t-pentylhydroquinone-di-octyl ether.

Eleven samples of multi-layered photographic material were prepared as above and each was processed as in Example 2. The specific types of the Y-coupler, M-coupler and C-coupler used, and the results of the photographic processing are shown in Table 3 below. Each of the samples was checked for its magenta density after exposure to white light. The specific sensitivity and light fastness were measured by the same methods as used in Example 1. The data in Table 3 show the improved light fastness of the dye images produced by using the magenta couplers prepared in accordance with the present invention. It was also clear that the light fastness of the images could be further improved by using UV absorbers in combination with the magenta couplers.

*Ultraviolet absorber

-continued
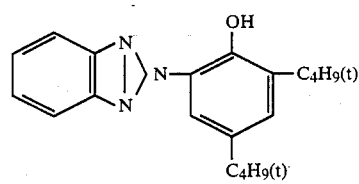 UV-1
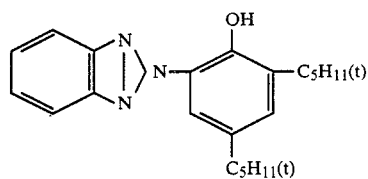 UV-2
*Y-couplers*
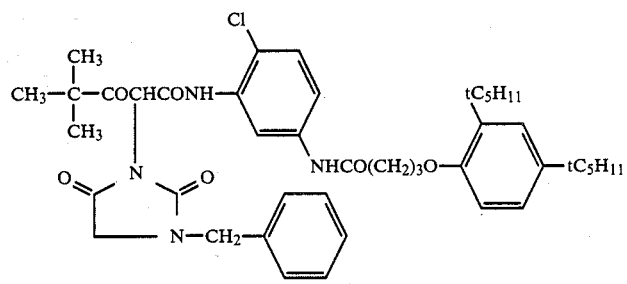 Y-1
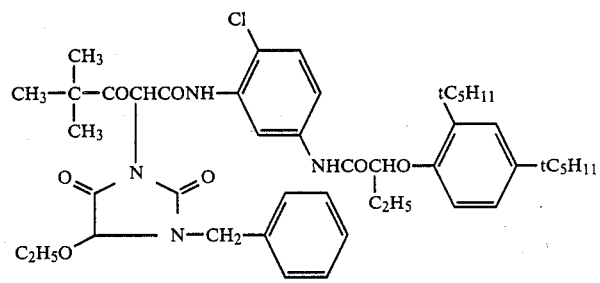 Y-2
*C-couplers*
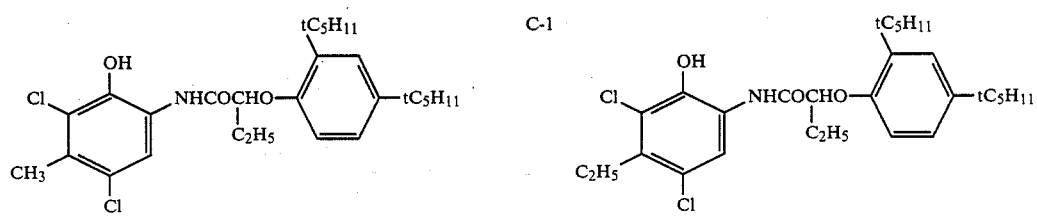
C-1        C-2
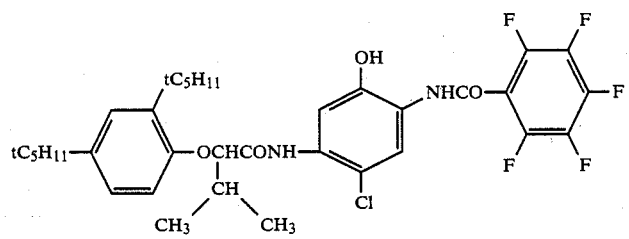 C-3
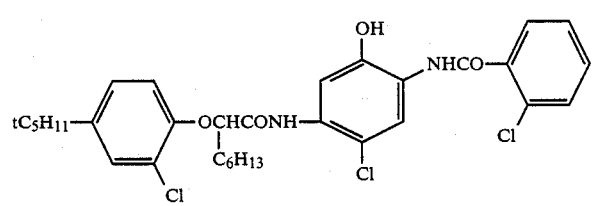 C-4
TABLE 3
| Sample No. | Layer (1) Y-coupler | Layer (3) M-coupler | Layer (5) C-coupler | Layer (5) UV-absorber | Specific sensitivity | Maximum density | Light fastness | Remarks |
|---|---|---|---|---|---|---|---|---|
| 3-31 | Y-1 | Comparative coupler (1) | C-1 | — | 100 | 2.30 | 22 | |

TABLE 3-continued

| Sample No. | Layer (1) Y-coupler | Layer (3) M-coupler | Layer (5) C-coupler | Layer (5) UV-absorber | Specific sensitivity | Maximum density | Light fastness | Remarks |
|---|---|---|---|---|---|---|---|---|
| 3-32 | Y-1 | Comparative coupler (1) | C-1 | UV-1 UV-2 | 101 | 2.27 | 35 | 2 mg of UV absorber in layer (5) |
| 3-33 | Y-1 | Coupler (12) of the invention | C-1 | — | 99 | 2.30 | 39 | |
| 3-34 | Y-1 | Coupler (12) of the invention | C-1 | UV-1 UV-2 | 102 | 2.26 | 50 | |
| 3-35 | Y-2 | Coupler (12) of the invention | C-2 | UV-1 UV-2 | 102 | 2.35 | 49 | |
| 3-36 | Y-2 | Coupler (12) of the invention | C-2 | UV-1 UV-2 | 101 | 2.38 | 57 | Another layer (2) inserted between layers (5) and (6) in sample No. 35 |
| 3-37 | Y-1 | Coupler (12) of the invention | C-3 | UV-1 UV-2 | 103 | 2.39 | 48 | |
| 3-38 | Y-1 | Coupler (12) of the invention | C-3 | UV-1 UV-2 | 99 | 2.32 | 56 | Same layer arrangement as in Sample No. 36 |
| 3-39 | T-2 | Coupler (12) of the invention | C-4 | UV-1 UV-2 | 97 | 2.32 | 47 | |
| 3-40 | Y-2 | Coupler (12) of the invention | C-1 | UV-1 UV-2 | 103 | 2.35 | 47 | |
| 3-41 | Y-1 | Coupler (11) of the invention | C-1 | UV-1 UV-2 | 102 | 2.37 | 51 | |

What is claimed is:

1. A silver halide color photographic material having at least one silver halide emulsion layer on a support, said silver halide emulsion layer containing at least one of the 1H-pyrazolo[3,2-c]-S-triazole derived magenta couplers that have a substituent of the following formula at 3-position:

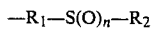

wherein
$R_1$ is an alkylene group;
$R_2$ is an alkyl, cycloalkyl or aryl group; and
n is 1 or 2.

2. A silver halide color photographic material according to claim 1, wherein said magenta coupler is one represented by the following formula:

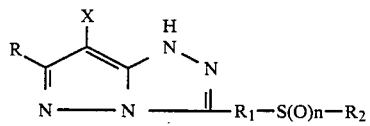

wherein
$R_1$ is an alkylene group;
$R_2$ is an alkyl, cycloalkyl or aryl group;
X is a leaving group which leaves upon reaction with the oxidation product of a color developing agent;
R is an alkyl, cycloalkyl, aryl or heterocyclic group; and
N is 1 or 2.

3. A silver halide color photographic material according to claim 2, wherein the alkyl group represented by R is a tertiary alkyl group.

4. A silver halide color photographic material according to claim 2, wherein the alkyl group represented by R is a tertiary butyl group.

5. A silver halide color photographic material according to claim 1, wherein n in the formula for said substituent is 1.

6. A silver halide color photographic material according to claim 2, wherein R in the formula for said magenta coupler is a secondary alkyl group, $R_1$ is an alkylene group having 3 to 6 carbon atoms in the straight chain, n is 2 and $R_2$ is an alkyl or cycloalkyl group.

7. A silver halide color photographic material according to claim 2, wherein X in the formula for said magenta coupler is a halogen atom.

8. A silver halide color photographic material according to claim 1, wherein said magenta coupler is the following compound:

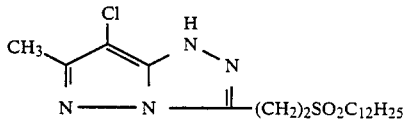

9. A silver halide color photographic material according to claim 1, wherein said magenta coupler is one selected from among the following three compounds:

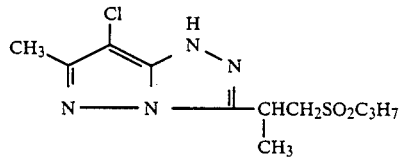

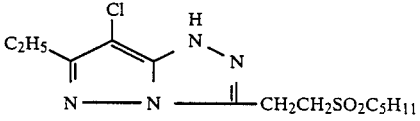

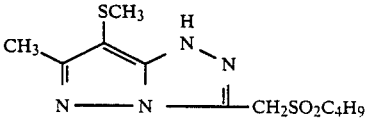

10. A silver halide color photographic material according to claim 1, wherein $R_1$ is an alkylene group having 1 to 6 carbon atoms.

11. A silver halide color photographic material according to claim 1, wherein $R_2$ is an alkyl or aryl group.

* * * * *